United States Patent [19]

Antwiler

[11] Patent Number: 5,057,226

[45] Date of Patent: * Oct. 15, 1991

[54] TREATMENT OF LIQUID INCLUDING BLOOD COMPONENTS

[75] Inventor: Glen D. Antwiler, Lakewood, Colo.

[73] Assignee: Cobe Laboratories, Inc., Lakewood, Colo.

[ * ] Notice: The portion of the term of this patent subsequent to Nov. 6, 2007 has been disclaimed.

[21] Appl. No.: 556,033

[22] Filed: Jul. 20, 1990

Related U.S. Application Data

[62] Division of Ser. No. 195,496, May 18, 1988, Pat. No. 4,968,432.

[51] Int. Cl.[5] .................... B01D 21/00; B01D 61/24
[52] U.S. Cl. .................................... 210/641; 210/645; 210/646; 210/651; 210/730; 210/731; 210/806; 530/380; 530/419; 530/830; 604/5; 604/6
[58] Field of Search ............... 210/634, 637, 645, 646, 210/650, 651, 729, 730, 731, 806; 604/4, 5, 6; 530/389, 418, 419, 421, 829, 830; 436/71, 175, 178

[56] References Cited

U.S. PATENT DOCUMENTS

| | | | |
|---|---|---|---|
| 3,519,558 | 7/1990 | Cooper et al. | 210/651 |
| 3,733,179 | 5/1973 | Guehler | 219/789 |
| 4,110,077 | 8/1978 | Klein et al. | 436/16 |
| 4,185,963 | 1/1980 | Heuck | 436/71 |
| 4,303,068 | 12/1982 | Zelman | 210/637 |
| 4,379,083 | 4/1983 | Falke et al. | 530/380 |
| 4,381,999 | 5/1983 | Boucher et al. | 210/637 |
| 4,486,341 | 12/1984 | Chang | 530/380 |
| 4,563,337 | 1/1986 | Kim | 210/638 |
| 4,746,605 | 5/1988 | Kerscher et al. | 436/175 |
| 4,770,784 | 9/1988 | Davis et al. | 210/638 |
| 4,923,439 | 5/1990 | Seidel et al. | 604/6 |
| 4,968,432 | 11/1990 | Antwiler | 210/637 |

Primary Examiner—W. Gary Jones

[57] ABSTRACT

A method of removing a constituent of a biological fluid including a blood component, said method including flowing the biological fluid past one side of a first semipermeable membrane, flowing solution containing a first precipitation agent past a second side of the membrane so as to cause transfer of the precipitation agent through the membrane to the biological fluid so as to improve precipitation characteristics of the fluid; and precipitating the constituent from the biological fluid. Also disclosed are maintaining a lower pressure in a biological fluid in a dialyzer than in dialysate at all portions of a membrane in the dialyzer and adding a continuously flowingy stream of concentrated precipitation agent to a continuously flowing stream of a biological fluid.

8 Claims, 1 Drawing Sheet

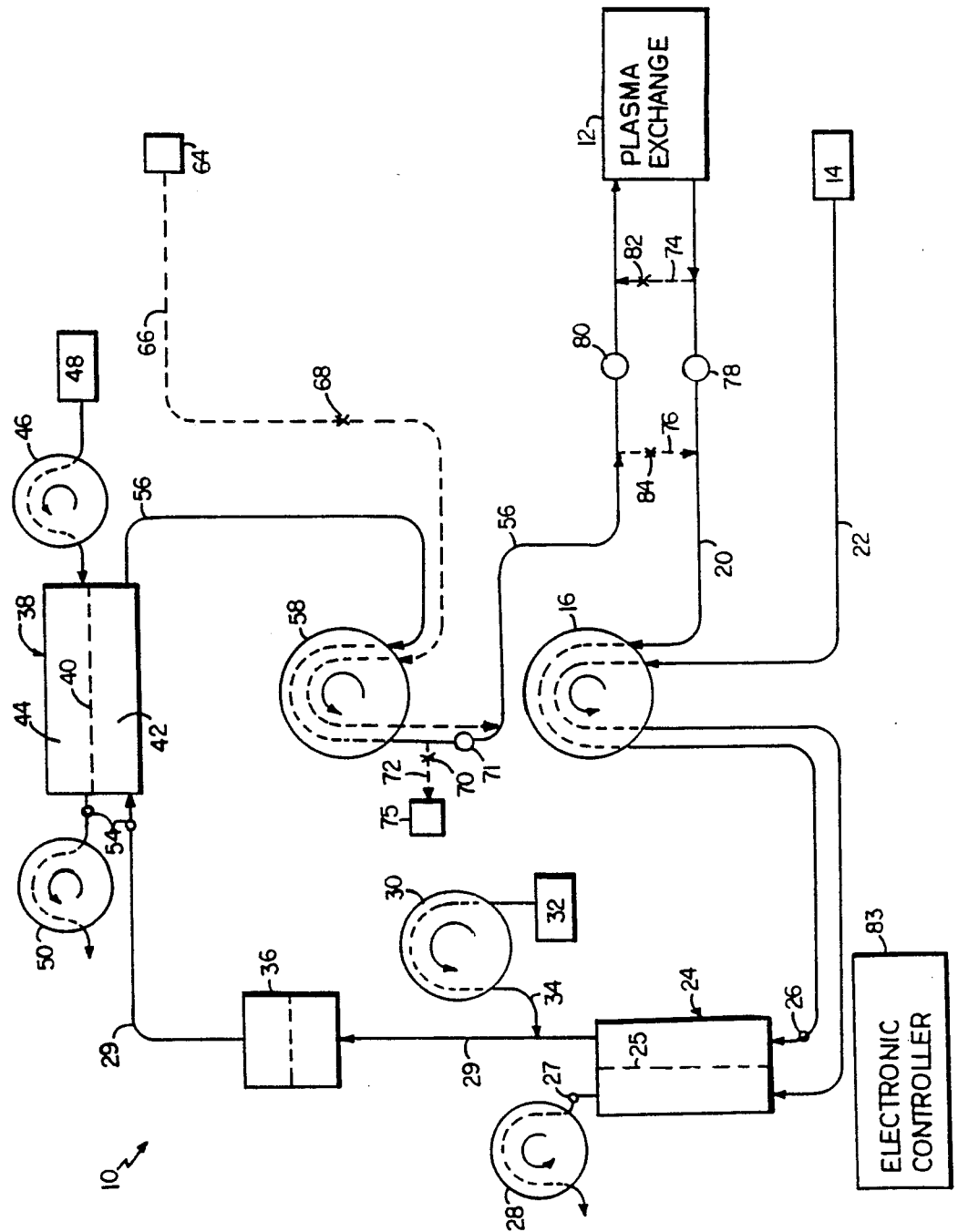

TREATMENT OF LIQUID INCLUDING BLOOD COMPONENTS

This application is a division, of application Ser. No. 195,496, filed May 18, 1988 now U.S. Pat. No. 4,968,432.

BACKGROUND OF THE INVENTION

The invention relates to treatment of liquid including blood components, e.g., the regeneration of plasma.

Low density lipoproteins (LDL's) and very low density lipoproteins (VLDL's) are present in the blood and have been implicated as a cause of coronary disease. A general method of removing LDL's and VLDL's from blood involves isolating the plasma portion of the blood, precipitating the LDL's and VLDL's present in the plasma, and filtering the plasma. The filtered plasma can be regenerated and subsequently returned to a patient.

SUMMARY OF THE INVENTION

In one aspect the invention features advantageously removing a constituent (e.g., LDL's and VLDL's) of a biological fluid (e.g., plasma) by flowing the fluid past one side of a semipermeable membrane, flowing a solution including a precipitation agent, the dialysate, past the other side of the membrane so as to cause the precipitation agent to transfer through the membrane into the biological fluid, and precipitating the constituent from the fluid. The precipitation agent is thus added to the biological fluid without causing a large increase in the volume of the fluid. The addition of the precipitating agent by this dialysis method also has the advantage of being able to control the concentration of the precipitating agent in the biological fluid by controlling its concentration in the dialysate. In preferred embodiments the precipitation agent includes divalent metal cations (e.g., $Mg^{+2}$ and $Ca^{+2}$); the constituents that are precipitated are LDL's and VLDL's; a second precipitation agent (preferably a sulfonated polyanion, most preferably a sulfonated polysaccharide, e g., dextran sulfate or heparin) is added to the biological fluid; and the precipitate is removed in a separator including a semipermeable membrane. This method is also useful in reducing the concentration of other components in the biological fluid, such as $Na^+$ and $K^+$.

In another aspect the invention features adding a precipitation agent (e.g., dextran sulfate) to a continuously flowing stream of a biological fluid without a large increase in the volume of the fluid by continuously adding an aqueous solution containing the agent at a flow rate that is less than 50% (preferably less than 20%, more preferably less than 10%, and most preferably less than 5% and around 1 to 3%) of the flow rate of the biological fluid.

In another aspect the invention features maintaining a lower pressure in a biological fluid (e.g., plasma to which dextran sulfate has been added) during dialysis than in the dialysate along all portions of a semipermeable membrane so that any ultrafiltrate flows from the dialysate to the biological fluid, thereby guaranteeing avoidance of increase in concentration of the fluid near the membrane, and avoiding undesirable precipitation or aggregation that might otherwise result from such an increase. In preferred embodiments there is an upstream dialyzer; and the transmembrane pressure is maintained below about $-5$ mm Hg.

Other advantages and features of the invention will be apparent from the following description of the preferred embodiment thereof and from the claims.

DESCRIPTION OF THE PREFERRED EMBODIMENT

The preferred embodiment will now be described

DRAWING

The FIGURE is a diagrammatic representation of a plasma regeneration system according to the invention.

STRUCTURE

Referring to the FIGURE, continuous plasma regeneration system 10 is used to regenerate plasma separated from a patient's blood by plasma exchange system 12 (e.g , a Century TPE system, available from Cobe Laboratories, Inc., Lakewood, Colo.). Plasma pump 16 is used to pump plasma from system 12 and a first precipitation agent solution containing divalent cations (e.g., $CA^{+2}$ and/or $Mg^{+2}$) and lacking $Na_+$ and $K^+$ from source 14 into the system at equal flow rates through lines 20 and 22, respectively. The plasma and the precipitation agent solution concurrently flow from lines 20 and 22 into dialyzer 24 (a hollow-fiber dialyzer available from Cobe Laboratories, Inc. under the HF140 trade designation). The two fluid flows in dialyzer 24 are separated by semipermeable membrane 25. (In fact there are a plurality of hollow fibers providing the semipermeable membrane defining the two flow paths.) Pressure sensors 26, 27 are used to provide pressure readings for dialyzer 24, in particular to determine the transmembrane pressure (TMP). The rate of flow of precipitation agent solution leaving dialyzer 24 is controlled by outlet pump 28.

Plasma flows from dialyzer 24 through line 29. A second precipitating agent solution (e.g., a solution of dextran sulfate (DxS) at a concentration of 1.6 gm/ml having an average molecular weight of 5,000) is pumped by pump 30 from source 32 through line 34 to combine with the plasma in line 29 to cause the precipitation of LDL's and VLDL's. The speed of pump 30 is controlled in an automated fashion so that the operator can select (and change) the amount of the second precipitating agent solution being added to the plasma The plasma flows through separator 36 (a filter having a microporous membrane, pore size 0.6 um), which removes precipitate from the plasma. The filtered plasma then flows into dialyzer 38 (another HF140 dialyzer), which includes semipermeable membrane 40 separating the plasma in compartment 42 from a counter-flowing dialysate in compartment 44. The dialysate is pumped into compartment 44 by inlet pump 46 from dialysate source 48. The dialysate delivery system for dialyzer 38 is as described in Boucher et al U.S. Pat. No. 4,381,999, which is hereby incorporated by reference. The dialysate delivery system controls TMP and thus ultrafiltration at dialyzer 38. Pressure sensors 54 associated with dialyzer 38 provide fluid pressure readings in order to determine inlet TMP.

The regenerated plasma flows from dialyzer 38 through line 56; return pump 58 controls the rate at which the regenerated plasma flows out of dialyzer 38 and, eventually, into plasma exchange system 12 for return to the patient. Pump 58 also acts on line 66 to optionally pump replacement fluid from source 64 to a location on line 56 downstream of collection line 72, used to direct regenerated plasma to collection bag 75 when alternate source 64 of replacement fluid is used. Clamps 68, 70, 71 control flow in lines 66, 72, 56, respectively, to switch between the normal and the collection modes, clamps 68 and 70 being closed and clamp 71 being open in the normal mode and vice versa in the collection mode.

Shunt lines 74 and 76 connect line 20 and line 56. In the event of an alarm condition, clamp 78 on line 20 and clamp 80 on line 56 are automatically closed, and clamps 82. 84 on lines 74, 76 are automatically opened, causing regenerated plasma to be recycled through line 20 and incoming plasma to be returned untreated to plasma exchange system 12.

An electronic control system, generally indicated as 83 in the FIGURE, automatically controls pumps 16, 28, 30, 58 and clamps 68, 70, 71, 78, 80, 82, 84 and receives pressure signals from pressure sensors 26, 27 and 54 (connections not shown).

OPERATION

The preferred use of plasma regeneration system 10 is to remove LDL's and VLDL's from plasma continuously flowing in line 20 by precipitation induced by separately adding precipitation agents at dialyzer 24 and through line 34 while removing other agents at dialyzer 24, removing the precipitate from the plasma at separator 36, and dialyzing the plasma at dialyzer 38 before returning the plasma to plasma exchange system 12 for return to the patient.

The first precipitating agent solution from source 14 includes the divalent cations $CA^{+2}$ and $Mg^{+2}$, which are transferred to the plasma in dialyzer 24 by perfusion across semipermeable membrane 25 while $Na_+$ and $K^+$ are dialyzed out of the plasma. The concentrations of divalent cations in the first precipitating agent solution and in plasma in dialyzer 24 equilibrate in travel through dialyzer 24 at equal flow rates, so that the concentrations tend to be equal at the outlets. In general, a first precipitating agent solution containing 90–110 mM calcium chloride and/or magnesium chloride raises the divalent cation concentration in the plasma to an appropriate level while lowering the concentration of $Na^+ + K^+$.

The second precipitating agent solution from source 32 includes DxS or another sulfonated polyanion (e.g., heparin), which is added through line 34 in the form of a concentrated solution in order to avoid significantly increasing the volume of the plasma. Generally, the amount of DxS or other polyanion added is selected based on the cholesterol concentration in the plasma. The following gives typical concentrations of DxS desired in the mixed plasma-precipitation agent solution for given concentrations of cholesterol: 300–450 mg % cholesterol:35 mg % DxS; 200–300 mg % cholesterol:30 mg % DxS; 150–200 mg % cholesterol:25 mg % DxS; 100–150 mg % cholesterol:20 mg % DxS; and less than 100 mg % cholesterol:15 mg % DxS. The DxS in solution from source 32 is sufficiently concentrated so that the flow rate of the solution added is less than 50% of the flow of plasma in line 29; preferably the flow rate is less than 20%, more preferably less than 10%, and most preferably less than 5% and about 1 to 3%. Increasing the concentration of DxS not only increases the effectiveness of removing LDL's plus VLDL's but also increases the concentration of DxS remaining in the plasma after precipitation. Using lower concentrations of DxS has the opposite effect. An advantage of limiting the volume of the plasma during precipitation is that it permits return to the patient of lower quantities of DxS, because the more concentrated LDL and VLDL can be precipitated more effectively, consuming the DxS.

The combination of divalent cations and sulfonated polyanions cause the LDL and VLDL in the plasma in line 29 to precipitate. Sulfonated polyanions (e.g., sulfonated polysaccharides such as DxS and heparin) are believed to bridge between LDL's (and also VLDL's), and the divalent cations are important in serving to form bridges between the charges of the polyanions and LDL's and VLDL's. It also is important to remove the monovalent cations so that they do not compete for the same sites as the divalent cations. As this process occurs, the LDL and VLDL in the plasma form complexes which become too large to remain in solution and thus precipitate. The plasma containing the precipitate flows through separator 36, where the precipitate is removed by filtration.

The plasma flows from separator 36 into dialyzer 38 (compartment 42), where plasma is dialyzed against a counter-flowing hemodialysis dialysate in compartment 44. The dialysate is pumped into compartment 44 by pump 46 and out of the compartment by pump 50; the flow rate is about 500 ml/min and is controlled by pumps 46 and 50. Return pump 58 controls the rate of regenerated plasma flow from dialyzer 38. To avoid the precipitation of proteins (e.g., fibrinogen and/or fibrin complex) in dialyzer 38, the inlet TMP in dialyzer 38 is not allowed to be greater than about −5.0 mm Hg. The inlet TMP is the TMP in dialyzer 38 at the point where the plasma flows into the dialyzer. The sign convention is chosen so that a negative TMP means that the pressure on the plasma side of the membrane (compartment 42) is less than the pressure on the dialysate side (compartment 44). Accordingly, a negative TMP provides a flux of fluid (ultrafiltrate) from the dialysate side of the membrane to the plasma side. Because the plasma in compartment 42 and the dialysate in compartment 44 are counter-flowing and pressure decreases during flow from the inlets to the outlets, the TMP becomes progressively less from the plasma inlet to the plasma outlet. A negative TMP is thus present throughout the dialyzer, avoiding a local increased concentration in the plasma at the membrane wall that could lead to the precipitation of plasma proteins. The use of dialyzer 24 permits dialyzer 38 to operate at a negative TMP, because such use permits limiting the volume of fluid added in conjunction with the addition of the precipitation agents (both the sulfonated polyanion and the divalent meta cation) so that there is no need to remove excess fluid from the plasma in dialyzer 38 by ultrafiltration; there is such a need in systems that add precipitating agents in a flow that is added to and equals the flow of plasma. (The divalent cations cannot be added in concentrated form, as they would form precipitates. Even if the calcium could be added in a concentrate, dialyzer 24 is desirable to (1) remove the $Na^+$ and $K^+$ and (2) remove fluid so that one could assure that dialyzer 38 can run at negative TMP.) Dialyzer 24 can be operated to remove liquid in the plasma to make up for the addition of liquid at dialyzer 38, if so desired by the operator to meet desired flows. If the fibrinogen and/or fibrin complex do form and precipitate, it is upstream of separator 36, and the precipitate is removed in separator 36.

The user generally operates system 10 in one of two basic modes by setting return pump 58 to run at a fixed (but adjustable) percentage of the rate of pump 16, which is generally operated between 30 and 40 ml/min with an upper limit of 50 ml/min. In the first mode, the flow of regenerated plasma out of the system approximately equals the flow of plasma into the system. In the second mode the flow of regenerated plasma out of the system is greater than the flow of plasma into the system. (It also is possible to return slightly less than the incoming flow, if so desired.)

In operating in the first mode, in order to provide a flow out that equals flow in, fluid is removed from the plasma in dialyzer 24 at a rate equal to the total flow rate of fluid added to the system in dialyzer 38 (owing to the negative TMP) and from adding the sulfonated polyanion solution through line 34. The direction and magnitude of ultrafiltration in dialyzer 24 are controlled by pump 28; the ultrafiltration is equal to the difference in flow rates between pump 16 and pump 28.

In operating in the second mode, if the excess flow of outflowing regenerated plasma is less than the flow of fluid added from line 34 and in dialyzer 38, fluid is once again removed from the plasma in dialyzer 24 by appropriate control of pump 28. If, as is more likely to be the case, the excess flow of regenerated plasma exceeds the flow rate of fluid from line 34 and in dialyzer 38, a flow of fluid equal to the difference is added to the plasma by ultrafiltration in dialyzer 24. In order to provide for a large range in the amount of fluid that can be added to the plasma in the second mode without going below a negative TMP value that would collapse the fibers (about $-200$ mm Hg for the HF140 dialyzer), a control scheme is employed that generally splits the addition of fluid between dialyzers 24, 38 by controlling the inlet TMP of dialyzer 38 (through control of pump 28) to match the TMP of dialyzer 24. This control of providing matching TMP's is used in both modes so long as the overriding constraint that inlet TMP at dialyzer 38 be less than $-5$ mm Hg is met.

Other Embodiments

Other embodiments of the invention are within the scope of the following claims. Other control schemes can be used, e.g., having other than matched TMP's at dialyzers 24, 38, so long as a lower limit is not crossed (e.g., $-200$ mm Hg), and positive TMP is avoided in dialyzer 38. It would also be acceptable for the TMP of dialyzer 38 to be positive, as long as the net ultrafiltration did not cause protein aggregation or precipitation. (A negative TMP assures this will not happen.) Other sulfonated polyanions, in particular other sulfonated polysaccharides, can be used in place of DxS. Flow through line 22 could be pumped independently of plasma by using a second pump, and there could be counter-current flow in dialyzer 24, in which case there would be a higher flow rate but lower concentration of divalent cation; this setup is presently the most preferred one.

What is claimed is:

1. A method of regenerating a biological fluid obtained from a patient's blood prior to return of the biological fluid to said patient, said method comprising
receiving a continuously flowing stream of said biological fluid obtained from said patient's blood,
continuously adding an aqueous solution comprising a precipitation agent at a first flow rate to said stream of said biological fluid to provide a combined stream,
said stream of biological fluid continuously flowing at a second flow rate,
said first flow rate being equal to or less than 10% of said second flow rate,
inducing the precipitation of said constituent by said precipitation agent so as to cause a precipitate,
filtering said precipitate from said combined stream so as to provide a continuously flowing filtered stream of said biological fluid, and
returning said continuously flowing filtered stream to said patient.

2. The method of claim 1, further comprising, subsequent to said filtering, flowing said biological fluid past one side of a semipermeable membrane while flowing dialysate past a second side of said membrane.

3. The method of claim 1 wherein said first flow rate is less than 5% of said second flowrate.

4. The method of claim 3 wherein said constituent comprises VLDL's of LDL's.

5. The method of claim 4 wherein said precipitating agent comprises a sulfonated polyanion.

6. The method of claim 5 wherein said sulfonated polyanion is a sulfonated polysaccharide.

7. The method of claim 5 wherein said sulfonated polysaccharide is DxS.

8. The method of claim 1 wherein said biological fluid comprises plasma.

* * * * *